(12) United States Patent
Gilmartin et al.

(10) Patent No.: US 11,571,317 B2
(45) Date of Patent: Feb. 7, 2023

(54) DEVICES AND METHODS FOR CONTROLLED DELIVERY OF A STENT

(71) Applicant: Boston Scientific Scimed, Inc., Maple Grove, MN (US)

(72) Inventors: Gary Gilmartin, Foxford (IE); Geraldine A. Toner, Raphoe (IE); Louis McNern, Donegal (IE); Martyn Folan, Loughrea (IE); Matthew Montague, Galway (IE); Carmel Ralph, Galway (IE); Maire Bhreathnach, Galway (IE); Enda Connaughton, County Galway (IE); Martin Hynes, Galway (IE)

(73) Assignee: Boston Scientific Scimed Inc., Maple Grove, MN (US)

( * ) Notice: Subject to any disclaimer, the term of this patent is extended or adjusted under 35 U.S.C. 154(b) by 170 days.

(21) Appl. No.: 16/275,799

(22) Filed: Feb. 14, 2019

(65) Prior Publication Data
US 2019/0247211 A1  Aug. 15, 2019

Related U.S. Application Data

(60) Provisional application No. 62/631,228, filed on Feb. 15, 2018.

(51) Int. Cl.
*A61F 2/966* (2013.01)
*A61M 25/01* (2006.01)
*A61F 2/95* (2013.01)

(52) U.S. Cl.
CPC ......... *A61F 2/966* (2013.01); *A61M 25/0113* (2013.01); *A61F 2/9517* (2020.05);
(Continued)

(58) Field of Classification Search
CPC .... A61F 2/966; A61F 2/9517; A61F 12/9661; A61F 12/9662; A61F 2/82; A61F 2002/9511; A61F 202/9528; A61F 2002/9534; A61F 2002/9623; A61F 2/95; A61F 2/954; A61F 2/962; A61M 25/0113;
(Continued)

(56) References Cited

U.S. PATENT DOCUMENTS 6,238,402 B1    5/2001  Sullivan, III et al.
7,758,625 B2    7/2010  Wu et al.
(Continued)

FOREIGN PATENT DOCUMENTS

WO    2012099732 A1    7/2012

OTHER PUBLICATIONS

International Search Report and Written Opinion for PCT/US2019/017982, dated May 24, 2019, 9 pages.

*Primary Examiner* — Richard G Louis
*Assistant Examiner* — Chima U Igboko
(74) *Attorney, Agent, or Firm* — Seager, Tufte & Wickhem, LLP

(57) ABSTRACT

The present disclosure relates generally to the field of medical devices. In particular, the present disclosure relates to devices and methods for controlled delivery of a stent, such as a self-expanding stent, and more particularly for controlling the full deployment of a stent in incremental steps from a sheath and for controlling the reconstrainment of a stent in incremental steps within a sheath.

15 Claims, 8 Drawing Sheets

(52) U.S. Cl.
CPC ............... *A61F 2002/9534* (2013.01); *A61M 2205/103* (2013.01)

(58) Field of Classification Search
CPC .... A61M 2002/9534; A61M 2205/103; A61M 2205/106; A61B 17/12118
See application file for complete search history.

(56) References Cited

U.S. PATENT DOCUMENTS

| | | | |
|---|---|---|---|
| 8,216,296 B2 | 7/2012 | Wu et al. | |
| 9,220,619 B2 | 12/2015 | Ramos et al. | |
| 9,375,337 B1 | 6/2016 | Longo et al. | |
| 9,724,224 B2 | 8/2017 | Gillick et al. | |
| 2010/0049313 A1* | 2/2010 | Alon | A61F 2/2418 623/2.11 |
| 2012/0172963 A1* | 7/2012 | Ryan | A61F 2/966 623/1.11 |
| 2013/0268049 A1 | 10/2013 | Munsinger et al. | |
| 2016/0135975 A1* | 5/2016 | Shimoyama | A61F 2/86 623/1.12 |
| 2016/0302951 A1 | 10/2016 | Gerdts et al. | |

\* cited by examiner

DEVICES AND METHODS FOR CONTROLLED DELIVERY OF A STENT

PRIORITY

This application claims the benefit of priority under 35 USC § 119 to U.S. Provisional Patent Application Ser. No. 62/631,228 filed Feb. 15, 2018, which is incorporated by reference herein in its entirety and for all purposes.

FIELD

The present disclosure relates generally to the field of medical devices. In particular, the present disclosure relates to devices and methods for controlled delivery of a stent, such as a self-expanding stent, and more particularly for controlling the full deployment of a stent in incremental steps from a sheath and for controlling the reconstrainment of a stent in incremental steps within a sheath.

BACKGROUND

Stents, such as self-expanding stents, may be inserted to a target location in a body lumen while constrained within a sheath. Once located at the target site, the stent may be deployed by retracting the sheath proximally without any restriction on the proximal movement of the sheath. Undesirable consequences of this delivery system may include poor control over the amount of proximal movement by a user while retracting the sheath. A user may accidentally deploy more of the stent than intended as a result of too much withdrawing force being applied to the sheath. For example, the entire stent may be accidentally deployed with one proximal pulling motion of the sheath. The sheath may also be prematurely retracted proximally past a point where reconstrainment is no longer possible. These issues may result in a premature deployment of the stent in an undesirable location. Additionally, the existing mechanisms for deploying stents may require more than one user to actuate the mechanism, or both hands of one professional may be required to deploy a stent.

It may therefore be desirable to increase the amount of control available to a user for delivering a stent, and/or reducing the number of users, or hands of a single user, needed for a procedure. It is with these considerations in mind that the improvements of the present disclosure may be advantageous.

SUMMARY

The present disclosure in various embodiments includes generally apparatuses, systems and methods for controlled delivery of stents. An exemplary device for controlled delivery of a stent may include a handle, an inner member disposed distal to the handle and configured to extend within a lumen of the stent, and a sheath extending about the inner member and operable with the inner member to constrain the stent therebetween. The handle may include a deployment assembly that includes a deployment member extending along a deployment axis and connected to the constraining sheath. The assembly may be operable to translate the deployment member in incremental steps along the deployment axis in a first direction to at least partially deploy the stent, and may be operable to translate the deployment member in incremental steps along the deployment axis in a second direction to at least partially constrain the stent within the sheath. An exemplary method of using such a device may include inserting a stent disposed on an inner member and constrained within a sheath into a patient to a deployment location. The sheath may be connected to an elongate deployment member and may be at least partially retracted proximally from about the stent, and/or the stent may be at least partially reconstrained within the sheath, in incremental strokes that correspond to proximal movement and distal movement of a deployment member along a deployment axis of the device, respectively. A single stroke may retract the sheath a distance less than a length of the stent and/or reconstrain the stent within the sheath a distance less than a length of the stent.

In one aspect, a device for controlled delivery of a stent, may include a handle. The device may include an elongate inner member having a proximal end and a distal end. The inner member may be disposed distal to the handle and may be configured to extend within a lumen of the stent. The device may include a constraining sheath having a proximal end and a distal end. The sheath may extend about the inner member and may be operable with the inner member to constrain the stent therebetween. A deployment assembly may be disposed within the handle. The deployment assembly may include an elongate deployment member having a proximal end, a distal end, and a deployment axis extending therealong. The distal end of the deployment member may be connected to the proximal end of the constraining sheath. The assembly may be operable to translate the elongate deployment member in incremental steps along the deployment axis in a first direction to at least partially deploy the stent, and may be operable to translate the deployment member in incremental steps along the deployment axis in a second direction to at least partially constrain the stent. The deployment assembly may include a drive gear configured to engage the elongate deployment member. The deployment assembly may include a drive shaft having a drive shaft axis perpendicular to the deployment axis. The drive shaft may be axially disposed through and coupled to the drive gear. A first gear may be axially disposed about and coupled to the drive shaft. A second gear may be axially disposed about and coupled to the drive shaft. The second gear may be spaced apart a distance from the first gear along the drive shaft axis. A reversing gear may be in communication with the second gear. A rack may be configured to alternately engage the first gear and the reversing gear. A first one-way bearing may be coupled to the first gear and may be axially disposed about and coupled to the drive shaft. The first bearing may be configured to prevent the first gear from imparting a rotary motion to the drive shaft that translates the deployment member in the first direction. A second one-way bearing may be coupled to the second gear and may be axially disposed about and coupled to the drive shaft. The second bearing may be configured to prevent the second gear from imparting a rotary motion to the drive shaft that translates the deployment member in the second direction. The rack may have a first length of teeth configured to engage the first gear. The rack may have a second length of teeth configured to engage the reversing gear. The first length and the second length may be parallel to the deployment axis and to each other. The first length may not be coplanar in height with the second length. The first length may be spaced apart from the second length a distance that is different than the distance between the first gear and the second gear, such that the rack can only alternately engage the first length with the first gear or the second length with the reversing gear. A cross-section of the rack in a plane normal to the deployment axis may be substantially L-shaped. The rack may be moveable back and forth along a first axis parallel to the drive shaft axis to alternately engage one of the first gear and the reversing gear. The rack may be moveable back and forth along a second axis parallel to the deployment axis to rotate one of the first gear and the reversing gear when alternately engaged therewith. The rack may include a pin extending outside of the handle. The pin may be engageable by a user to move the rack along the first axis. The rack may include a trigger extending outside of the handle. The trigger may be engageable by a user to move the rack along the second axis. Movement of the rack along the second axis in a proximal direction when engaging the first gear may translate to movement of the deployment member in the second direction. Movement of the rack along the second axis in a proximal direction when engaging the reversing gear may translate to movement of the deployment member in the first direction. The trigger may be a pistol-type trigger that may be pulled proximally by a user to move the rack in the proximal direction. The trigger may be a seesaw-type trigger that may rotate about a fulcrum. The trigger may rotate from above the fulcrum and may move the rack in the proximal direction. The trigger may rotate from below the fulcrum and may move the rack in a distal direction along the second axis. The trigger may be a thumb wheel that may be rotated by a user to move the rack in the proximal direction. The rack may be moveable in the proximal direction along the second axis a predetermined stroke length. The stroke length may be less than the length of the stent. The trigger may have a starting position. The deployment assembly may further comprise one or more springs cooperatively engaged with the rack to apply a biasing force onto the rack to return the trigger to the starting position. The drive gear and the elongate deployment member may each comprise teeth configured to engage each other. The first direction may be proximally along the deployment axis and the second direction may be distally along the deployment axis. Translating the elongate deployment member in the first direction may at least partially deploy the stent from within the sheath. Translating the elongate deployment member along the deployment axis in the second direction may at least partially constrain the stent within the sheath. The first direction may be proximal movement of the deployment member along the deployment axis and the second direction may be distal movement of the deployment member along the deployment axis. The inner member and the sheath may be integral to the handle. The inner member and sheath may be removably attached to the handle. The inner member may extend within the handle. The sheath may include a sheath lumen and the inner member may extend coaxially within the sheath lumen. A proximal end of the inner member may be fixed to the handle. The inner member may be configured to hold the stent in place relative to movement of the sheath. The deployment member may be one of removably connected to the sheath, fixedly connected to the sheath, or integral with the sheath. The deployment member may include a deployment member lumen coaxial with the sheath lumen. The inner member may extend coaxially through the deployment member.

In another aspect, a system for controlled stent delivery may include a self-expanding stent. The system may include an elongate inner member having a proximal end and a distal end. The inner member may be disposed distal to the handle and may be configured to extend within a lumen of the stent. The system may include a constraining sheath having a proximal end and a distal end. The sheath may extend about the inner member and may be operable with the inner member to constrain the stent therebetween. The system may include a handle containing a deployment assembly. The deployment assembly may include an elongate deployment member having a proximal end, a distal end, and a deployment axis extending therealong. The distal end of the deployment member may be connected to a proximal end of the constraining sheath. The assembly may be operable to translate the deployment member in incremental steps along the deployment axis in a first direction to at least partially deploy the stent, and may be operable to translate the deployment member in incremental steps along the deployment axis in a second direction to at least partially constrain the stent. The deployment assembly may include a drive gear configured to engage the elongate deployment member. The system may include a drive shaft, having a drive shaft axis perpendicular to the deployment axis. The drive shaft may be axially disposed through and coupled to the drive gear. A first gear may be axially disposed about and coupled to the drive shaft. A second gear may be axially disposed about and coupled to the drive shaft. The second gear may be spaced apart from the first gear along the drive shaft axis. A reversing gear may be in communication with the second gear. A rack may be configured to alternately engage the first gear and the reversing gear. A trigger may be configured to translate the rack proximally and distally. The rack may be disposed on a pin that is engageable by a user from outside of the handle. The system may include a first one-way bearing coupled to the first gear and axially disposed about and coupled to the drive shaft. The first bearing may be configured to prevent the first gear from imparting a rotary motion to the drive shaft that translates the deployment member in the first direction. A second one-way bearing may be coupled to the second gear and axially disposed about and coupled to the drive shaft. The second bearing may be configured to prevent the second gear from imparting a rotary motion to the drive shaft that translates the deployment member in the second direction. The rack may have a first length of teeth configured to engage the first gear and a second length of teeth configured to engage the reversing gear. The first length and the second length may be parallel to the deployment axis and to each other. The first length may not be coplanar in height with the second length. A cross-section of the rack in a plane normal to the deployment axis may be substantially L-shaped. The rack may be moveable back and forth along a first axis parallel to the drive shaft axis to alternately engage one of the first gear and the reversing gear. The rack may be moveable back and forth along a second axis parallel to the deployment axis to rotate one of the first gear and the reversing gear when alternately engaged therewith. The trigger may have a starting position. The deployment assembly may include one or more springs cooperatively engaged with the rack to apply a biasing force in a distal direction onto the rack to return the trigger to the starting position. The drive gear and the deployment member may each comprise teeth configured to engage each other. The rack may include a trigger extending outside of the handle. The trigger may be engageable by a user to move the rack along the second axis. Movement of the rack along the second axis may be in a proximal direction when engaging the first gear, which may translate to movement of the deployment member in the second direction. Movement of the rack along the second axis may be in a proximal direction when engaging the reversing gear, which may translate to movement of the deployment member in the first direction. The rack may be moveable in the proximal direction along the second axis a predetermined stroke length. The stroke length may be less than the length of the stent.

In another aspect, a method of delivering a stent may include inserting a stent into a patient to a deployment location. The stent may be disposed on an inner member and constrained within a sheath. The sheath may have a proximal end connected to an end of an elongate deployment member. The deployment member may extend along a deployment axis. The sheath may be at least partially retracted proximally from about the stent in incremental strokes, which may correspond to proximal movement of the deployment member along the deployment axis. A single stroke may retract the sheath a distance less than a length of the stent. Retracting the sheath from about the stent may include moving a rack proximally along an axis parallel to the deployment axis. The rack may communicate with one or more gears to transfer the proximal movement of the rack, through rotation of the gears, to the proximal movement of the deployment member. The stent may be at least partially reconstrained within the sheath in incremental strokes, which may correspond to a distal movement of the deployment member along the deployment axis. A single stroke may reconstrain the stent within the sheath a distance less than a length of the stent. Reconstraining the stent within the sheath may include moving a rack proximally along the axis parallel to the deployment axis. The rack may communicate with one or more gears to transfer the proximal movement of the rack, through rotation of the gears, to the distal movement of the deployment member. Retracting the sheath and reconstraining the stent within the sheath by the same proximal movement of the rack may include switching the rack from engaging one gear of the one or more gears to engaging another gear of the one or more gears. Retracting the sheath and reconstraining the stent within the sheath may be performed by movement of a trigger that is in communication with the rack. The trigger may be a pistol-type trigger, thumb wheel, or seesaw-type trigger. The deployment member may be removably connected to the sheath, fixedly connected to the sheath or integral with the sheath.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

Figure 1:
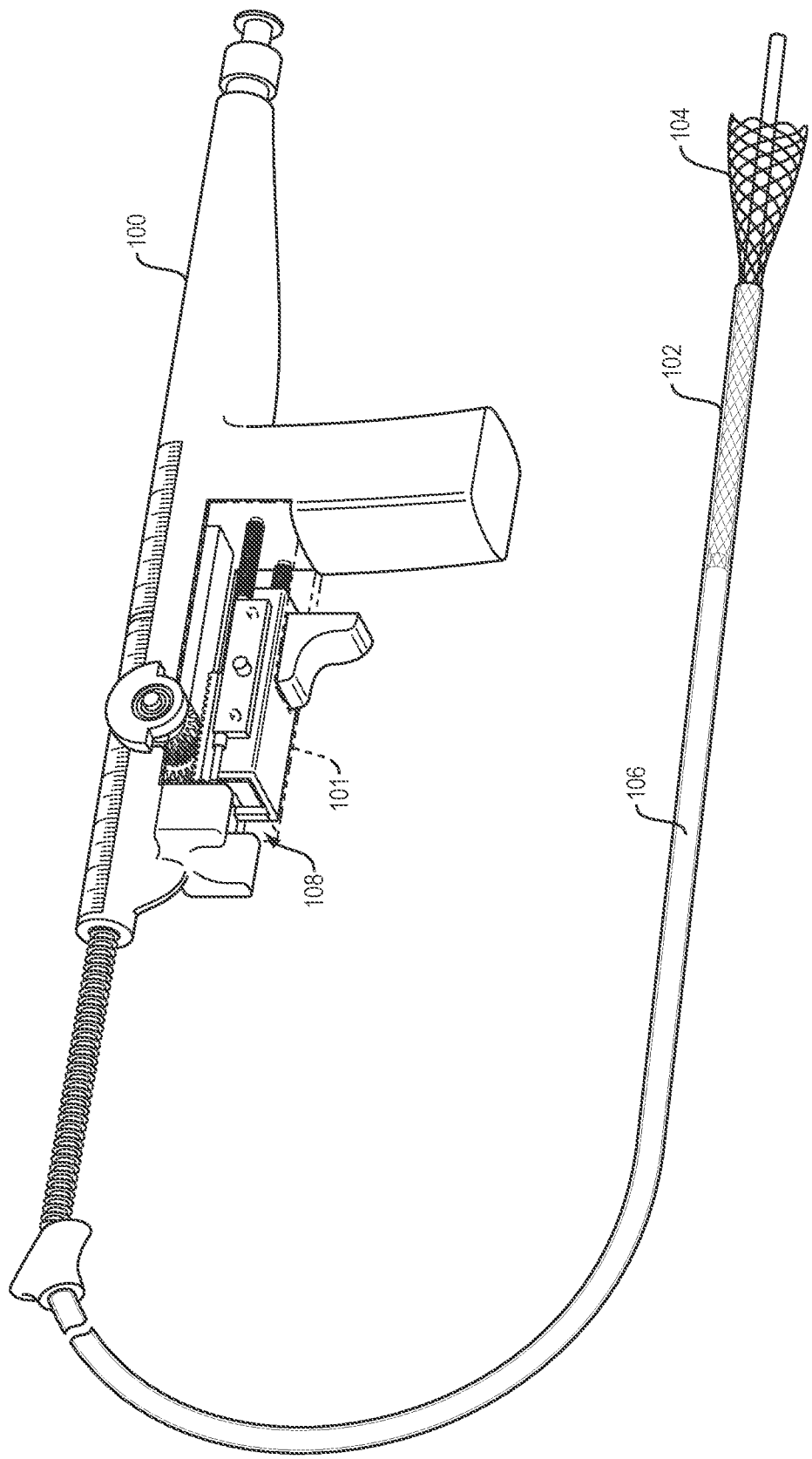
FIG. 1 illustrates a device delivering a self-expanding stent, in accordance with an embodiment of the present disclosure.

The present disclosure is not limited to the particular embodiments described. The terminology used herein is for the purpose of describing particular embodiments only, and is not intended to be limiting. Unless otherwise defined, all technical terms used herein have the same meaning as commonly understood by one of ordinary skill in the art to which the disclosure belongs.

Although embodiments of the present disclosure are described with reference to a "stent", it should be appreciated that a variety of other devices may be configured for controlled delivery in accordance with the present disclosure. Examples of such devices include devices for vena cava biopsies, suturing devices, snares forceps, and the like. In practice, any device or procedure that may benefit from controlled delivery and release could be used with embodiments of this disclosure.

Although embodiments of the present disclosure are described with reference to a "body lumen", it should be appreciated that a "body lumen" may refer to a variety of organs, systems, tracts, vessels, and/or cavities, such as the gastrointestinal system, vascular system, urogenital system, lymphatic system, neurological system, and the like.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

As used herein, the conjunction "and" includes each of the structures, components, features, or the like, which are so conjoined, unless the context clearly indicates otherwise, and the conjunction "or" includes one or the others of the structures, components, features, or the like, which are so conjoined, singly and in any combination and number, unless the context clearly indicates otherwise.

As used herein, the term "distal" refers to the end farthest away from the medical professional when introducing a device into a patient, while the term "proximal" refers to the end closest to the medical professional when introducing a device into a patient.

Embodiments of the present disclosure include devices, systems and method used to provide controlled delivery of a stent. A stent may be within a constraining sheath that is about the stent. A portion of the stent may be in a constrained configuration while within the sheath and a portion of the stent may be in an unconstrained configuration while outside of the sheath. The stent may be self-expanding and include a lumen extending therethrough that is of a constant or varying diameter. The stent may be configured in any manner of shape depending on the application and may include a retention member (e.g., flare or flange) on the distal and/or proximal end of the stent. The stent may be woven or knitted out of multiple filaments or a single filament and may include a single weave or knitted pattern throughout the stent, or the pattern may vary. A filament may have a variety of cross-sectional shapes, e.g., round, oval, rectangular, etc. A filament may comprise a shape memory material such as nitinol, platinol, a shape memory polymer, or the like. The stent may be comprised of a biocompatible metallic or polymeric material. The stent may be coated or covered with a polymeric material along the entire length and circumference of the stent or along portions of the length or circumference of the stent, or both. Non-polymeric coating material may alternatively be used. Suitable coating materials include, for instance, polymeric materials, drug-infused polymeric materials (including therapeutic agents, e.g., sirrolumus, everolimus, paclitaxel, anti-inflammatories, and the like), such as polytetrafluoroethylene or silicone rubbers, polyurethanes, polyvinylidene fluoride, polyethylene terephthalate, polymethyl methacrylate, poly lactic-co-glycolic acid, or ChronoFlex®, which are known to be biocompatible. A stent may be configured in a variety of dimensions depending on, for example, the medical use and/or the anatomy in which it is being used. For example, a stent for endoscopic use may have a diameter in the range of about 5 mm to about 30 mm, and may have a length of about 5 mm to about 200 mm.

Embodiments of the present disclosure may include a constraining sheath that may be moveable over a stent to deploy the stent from the sheath and/or reconstrain the stent within the sheath. The sheath may contain the stent within the sheath in a constrained configuration during insertion into a body lumen. The constrained configuration may include a reduced profile of the stent. Once the sheath and constrained stent are in a desired location, the sheath may be moved proximally over the stent to initiate deployment of the stent from a constrained configuration to an unconstrained configuration (for example, in the case of a self-expanding stent comprised of shape memory material, from an unexpanded stressed configuration to an expanded unstressed configuration). The sheath may be moved distally over the stent to reconstrain at least a portion of the stent within the sheath in the constrained (e.g., unexpanded) configuration. A constraining sheath may have a proximal end and a distal end, and may extend about an elongate inner member. The sheath may have a lumen along the length of the sheath with the inner member extendable coaxially within the sheath lumen. The sheath may be operable with the inner member to constrain the stent therebetween. A sheath may be integral with a handle or the sheath may be removably attached to the handle. A sheath may be connected with a deployment member or the sheath may be integral with the deployment member. A deployment member may be removably connected or fixedly connected with a sheath. A lumen of the sheath may be co-axial with a lumen of the deployment member.

Embodiments of the present disclosure may include an inner member. The inner member may be disposed distal to a handle and configured to extend within a lumen of a stent. The inner member may be configured to hold the stent in place with respect to relative movement of the sheath proximally and distally about the stent and inner member. The inner member may extend along the length of the sheath and may be flexible to assist in guiding the sheath and stent while inserting the stent to a target site in a body lumen. The inner member may be fixed in position relative to a handle of a device (e.g., a proximal end of the inner member by fixed within the handle housing), such that a proximal or distal movement of the sheath with respect to the inner member (and the handle, when the inner member is fixed thereto) will translate into proximal or distal movement of the sheath along the stent. The inner member may include at least one barb, fin, step-down, band, holder, hook, tine, or the like to retain the stent until the stent is fully deployed. The inner member may extend through an elongate deployment member, extend adjacently along the elongate deployment member, extend adjacently along the handle, extend within the handle, and/or extend away from the handle. The deployment member may include a deployment member lumen coaxial with the sheath lumen, and the inner member may extend coaxially through the deployment member. An inner member may include a lumen extending along the length of the inner member. Other medical instruments or devices may be disposed and/or extended through the lumen of the inner member to access a deployment site, such as a guidewire, or the lumen may be used to inject materials to the site, such contrast for imaging, therapeutic agents, etc. An inner member and constraining sheath, with or without a stent loaded therebetween, may be of a conventional delivery system with handle(s) that are capable of being retrofit with a device, and used in a procedure, in accordance with embodiments of the present disclosure. Alternatively, embodiments of the disclosure may be an inner member and sheath, with or without a stent loaded therebetween, that is configured as a standalone disposable that may be removably attached to a handle and deployment member of a device, which may be reusable. As a further alternative, embodiments of the disclosure may be an inner member and a sheath, with or without a stent loaded therebetween, that is configured integral with or fixedly connected to a handle and deployment member, as a complete device and system, which may be disposable as a whole after use.

With reference to FIG. 1, an embodiment of a device and system for controlled delivery of a stent according to the present disclosure is illustrated. The device may be configured for use with stent, or a system may include a device and a stent 104, pre-loaded or loadable on the device. The stent 104 is shown partially deployed with a distal portion of the stent in an unconstrained configuration and a proximal portion of the stent in a constrained configuration. The portion of the stent 104 in the constrained configuration is within a constraining sheath 102. An elongate inner member 106 extends within a lumen of the stent 104 and may extend some distance beyond the distal end of the stent. The inner member 106 extends along the length of the sheath 102. A deployment assembly 108 is disposed within a handle 100 and within a deployment assembly portion 101 of the handle 100 that is illustrated in phantom lines. Similar deployment assembly portions 101 of a handle 100 may be included with other embodiments described herein and otherwise within the scope of the disclosure. A proximal end of the inner member may be fixed in position relative to the handle and terminate in a luer fitting, as shown, at the proximal end of the handle. A lumen may extend through the inner member and communicate co-axially with an aperture in the luer fitting for purposes of receiving instruments and/or materials or fluids through the lumen to a deployment location.

Figure 2:
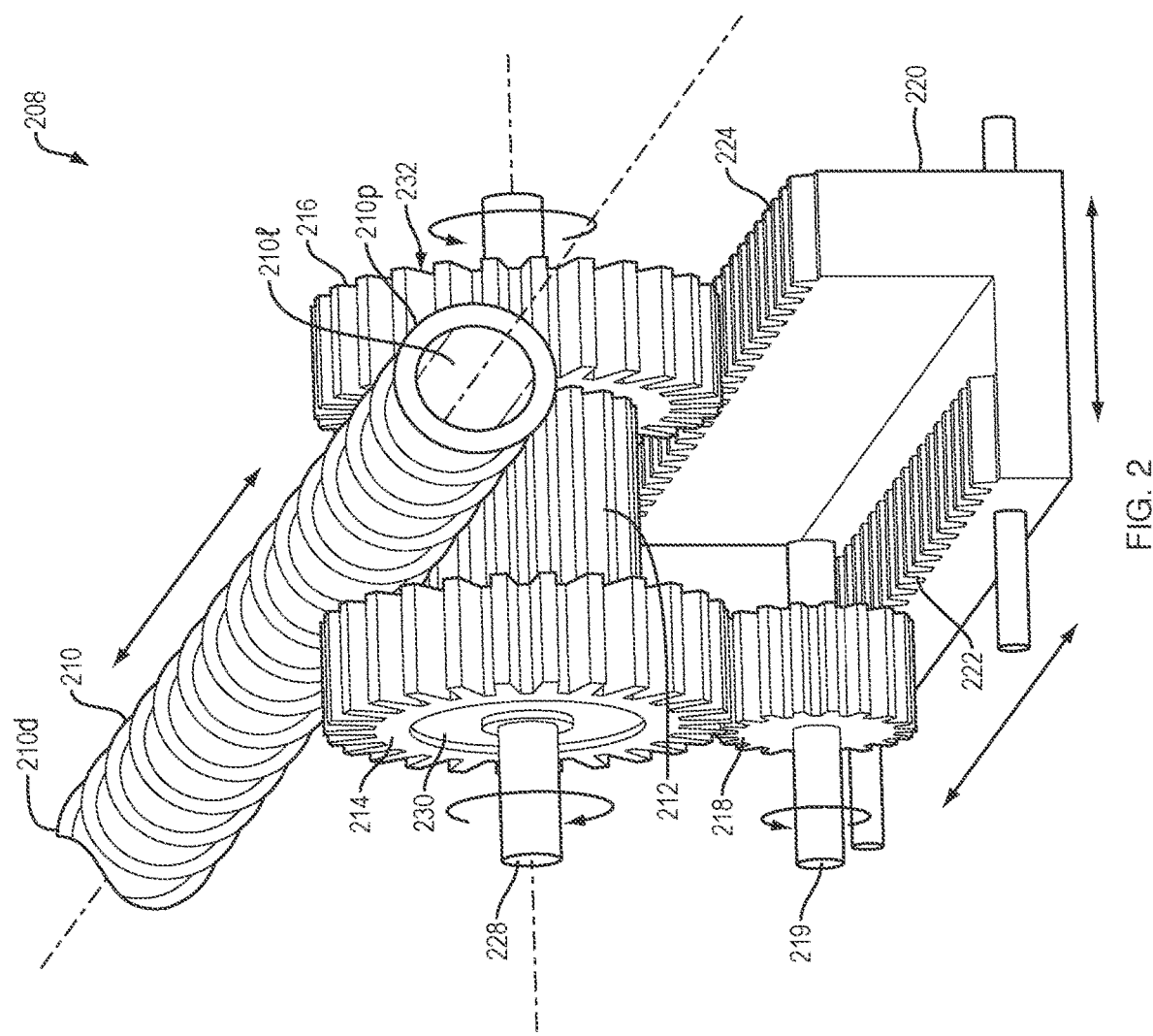
FIG. 2 illustrates a perspective view of a deployment assembly, in accordance with an embodiment of the present disclosure.

With reference to FIG. 2, an embodiment of a deployment assembly 208, as part of a device or system of the present disclosure, such as the assembly 108 within the handle 100 of the device in FIG. 1, is illustrated. An elongate deployment member 210 of the assembly has a proximal end 210p, a distal end 210d, an inner lumen 210l extending therethrough, and a deployment axis extending therealong from the proximal end 210p and the distal end 210d. The distal end 210d may be connected to a proximal end of a constraining sheath. The assembly 208 is operable to translate the elongate deployment member 210 in incremental steps along the deployment axis in a first direction (e.g., proximally) to at least partially unconstrain and/or deploy a stent that may be disposed on an inner member and constrained between the inner member and the sheath. A drive gear 212 is configured to engage the elongate deployment member 210. The drive gear 212 and the elongate deployment member 210 each have teeth configured to engage each other, such that rotation of the drive gear imparts translational movement to the deployment member along the deployment axis. Although teeth are shown, other ways may be envisioned to engage the drive gear and deployment member to achieve a similar arrangement and movement. A drive shaft 228, having a drive shaft axis perpendicular to the deployment axis, is axially disposed through and coupled to the drive gear 212. A first gear 216 is axially disposed about and coupled to drive shaft 228. A second gear 214 is axially disposed about and coupled to the drive shaft 228, and is spaced apart a distance from the first gear 216 along the drive shaft 228. A reversing gear 218 is disposed about pin 219. The reversing gear 218 has teeth that are engaged with teeth on the second gear 214, such that rotation of the reversing gear imparts a reverse rotation of the second gear (see arrows in FIG. 2), which imparts translational movement to the deployment member along the deployment axis. A first one-way bearing 232 is coupled to the first gear 216. The first one-way bearing 232 is axially disposed about and coupled to the drive shaft 228 and is configured to prevent the first gear 216 from imparting a rotary motion to the drive shaft 228 that translates the deployment member 210 in a first direction (e.g., proximally). A second one-way bearing 230 is coupled to the second gear 214. The second one-way bearing 230 is axially disposed about and coupled to the drive shaft 228 and is configured to prevent the second gear 214 from imparting a rotary motion to the drive shaft 228 that translates the deployment member 210 in a second direction (e.g., distally). A rack 220 is configured to alternately engage the first gear 216 and the reversing gear 218. The rack 220 has a first length of teeth 224 configured to engage the first gear 216 and a second length of teeth 222 configured to engage the reversing gear 218. The first length 224 and the second length 222 are parallel to the deployment axis and to each other. The first length of teeth 224 is not coplanar in height with the second length of teeth 222. A cross-section of the rack 220 in a plane normal to the deployment axis is substantially L-shaped. This allows the first length of teeth 224 to engage the first gear 216 closer to the drive shaft axis and the second length of teeth 222 to engage the reversing gear 218, which is situated farther from the drive shaft axis. The rack 220 is configured to alternately engage the first gear 216 and the reversing gear 218, but not at the same instant. In FIG. 2, the first length of teeth 224 is shown engaging the first gear 216, while the second length of teeth 222 is not engaging the reversing gear 218. The rack 220 alternately engages one of the first gear 216 and the reversing gear 218 because the first length of teeth 224 is spaced apart a distance from the second length of teeth 222 that is different than a distance between the first gear 216 and the second gear 214. The assembly 208 may be within a housing, with the shaft 228 and pin 219 having at least one end extending into the housing and being able to rotate freely within the housing. In various embodiments, the pin may be a T-shaped pin that is connected to a side of the housing only at one end of the pin. The rack 220 is moveable back and forth within the housing of the handle along a first axis parallel to the drive shaft axis to alternately engage one of the first gear 216 and the reversing gear 218. The rack 220 includes a pin 226 extending outside of the handle 200. The pin 226 is engageable by a user to move the rack along the first axis. The rack 220 is moveable back and forth along a second axis parallel to the deployment axis to rotate one of the first gear 216 and the reversing gear 218 when alternately engaged therewith. With this arrangement of a deployment assembly, the movement of the rack 220 may be controlled and may have a predetermined stroke length so as to move the deployment member 210 and an attached constraining sheath a distance less than the length of the stent. The first length of teeth 224 of the rack 220 may engage the first gear 216. Proximal movement of the rack 220 and the first length of teeth 224 while engaging the first gear 216 rotates the first gear 216 and the drive shaft 228 in the direction of the arrow near the first gear such that the drive gear 212 translates the deployment member 210 distally. The sheath connected to the deployment member is moved distally a distance that reconstrains a portion of a stent that has been partially deployed. A return stroke of the first length of teeth 224 and the rack 220 in a distal direction while engaged with the first gear 216 rotates the first gear 216 in a direction opposite of the arrow near the first gear 216. This opposing rotation of the first gear 216 is not translated to the drive shaft 228 because of the first one-way bearing 232. This movement may be repeated, as desired, to further reconstrain the stent within the sheath. The second length of teeth 222 of the rack 220 may engage the reversing gear 218 that is engaged with the second gear 214. Proximal movement of the rack 220 and the second length of teeth 222 while engaging the reversing gear 214 rotates the reversing gear 218 in the direction of the arrow nearest the reversing gear 218. The reversing gear 218 rotates the second gear 214 and the drive shaft 228 in the direction of the arrow nearest the second gear 214 such that the drive gear 212 translates the deployment member 210 proximally. The sheath connects to the deployment member, is retracted or moved proximally a distance that deploys or unconstrains a portion of the stent from within the sheath. A return stroke of the second length of teeth 222 and the rack 220 in a distal direction while engaged with the reversing gear 218 rotates the second gear 214 in a direction opposite of the arrow nearest the second gear 214. This opposing rotation of the second gear 214 is not translated to the drive shaft 228 because of the second one-way bearing 230. This movement may be repeated, as desired, to further deploy the stent.

Figure 3A:
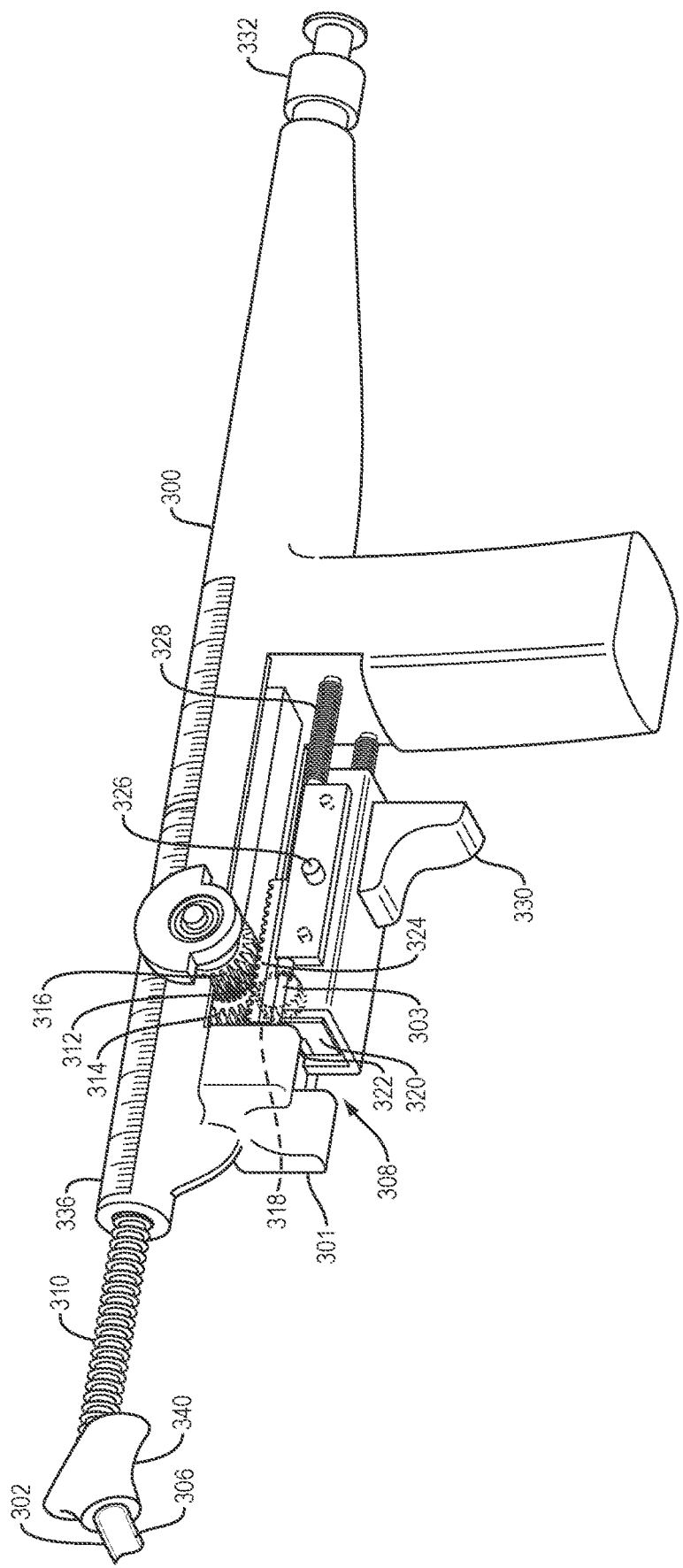
FIG. 3A illustrates a device having a handle and a deployment assembly with a pistol-type trigger, in accordance with an embodiment of the present disclosure.
Figure 3B:
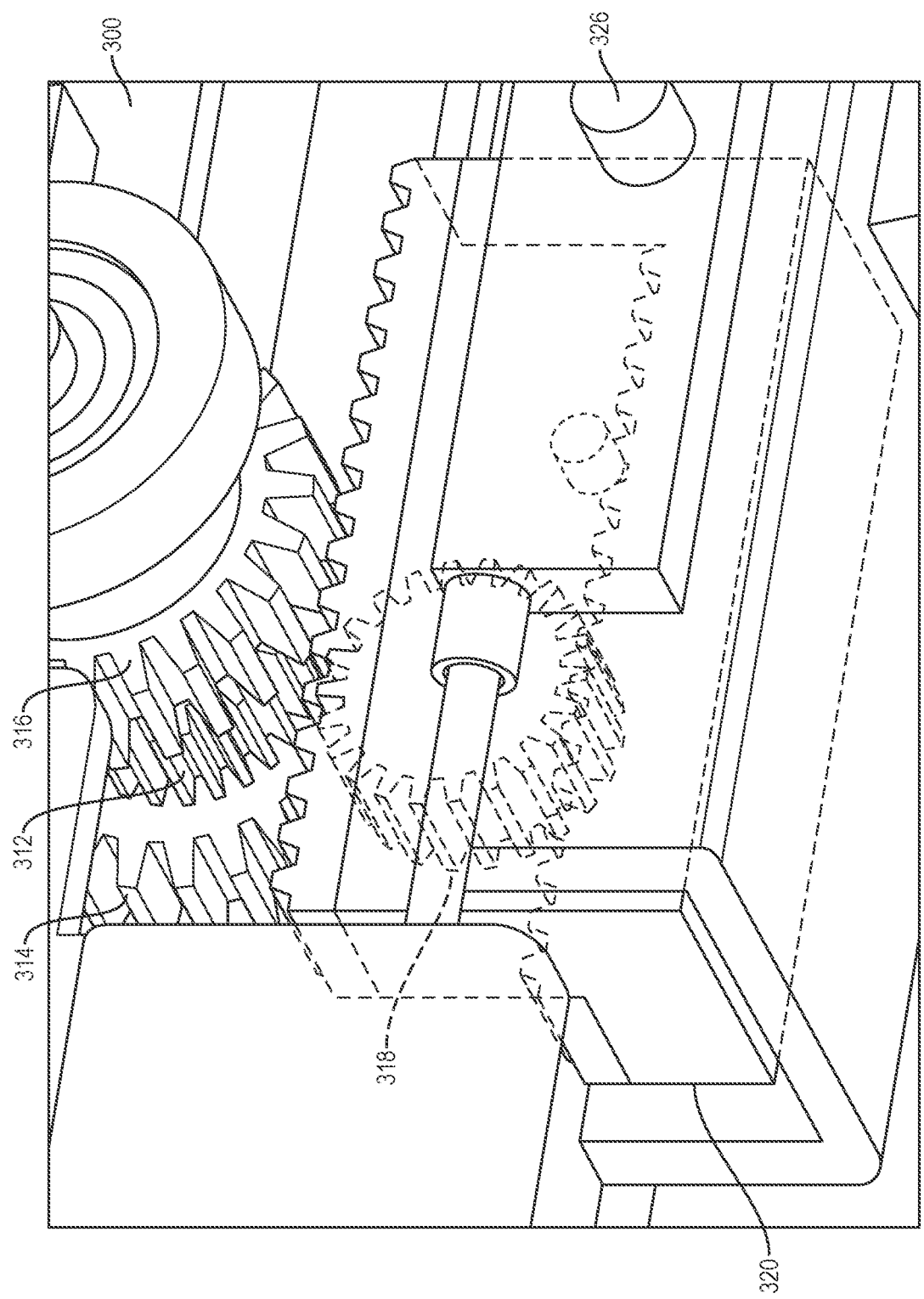
FIG. 3B illustrates a section of the device of FIG. 3A.

With reference to FIGS. 3A and 3B, an embodiment of a device for controlled delivery of a stent according to the present disclosure is illustrated, which includes a handle 300 containing a deployment assembly 308 disposed within the handle 300. The deployment assembly 308, which may be configured similarly to the gear and rack arrangement described with reference to FIG. 2, includes an elongate deployment member 310 with a proximal end, a distal end, an inner lumen therethrough, and a deployment axis extending therealong. The distal end of the elongate deployment member 310 is connected to a proximal end of a constraining sheath 302 via a connection member 340. The connection member 340 is shown as ergonomically shaped for a user to grab hold of it with their hand, should the user desire rapid deployment or reconstrainment. The connection member 340 may be used to rapidly unconstrain or reconstrain the stent by manually moving the connection member 340 proximally or distally. The user may rapidly move the connection member 340 while the rack 320 is engaged with a reversing gear 318 or a first gear 316 so long as the drive gear 312 is rotated by the deployment member 310 such that the drive shaft does not transfer rotation to the first gear 316 or a second gear 314 via the one-way bearings. The assembly 308 is operable to translate the elongate deployment member 310 in incremental steps along the deployment axis in a first direction (e.g., proximally) to at least partially deploys a stent constrained between an inner member 306 and the sheath 302. The assembly 308 is also operable to translate the deployment member 310 along the deployment axis in a second direction (e.g., distally) to at least partially constrain the stent. The assembly 308 also includes a drive gear 312 configured to engage the elongate deployment member 310. A drive shaft, having a drive shaft axis perpendicular to the deployment axis, is axially disposed through and coupled to the drive gear 312. A first gear 316 is axially disposed about the drive shaft. A second gear 314 is axially disposed about the drive shaft and spaced apart a distance from the first gear 316 along the length of the drive shaft. A first one-way bearing is coupled to the first gear 316. The first one-way bearing is axially disposed about and coupled to the drive shaft and is configured to prevent the first gear 316 from imparting a rotary motion to the drive shaft that translates the deployment member 310 in the first direction. A second one-way bearing is coupled to the second gear 314. The second one-way bearing is coupled to the drive shaft and is configured to prevent the second gear 314 from imparting a rotary motion to the drive shaft that translates the deployment member 310 in the second direction. A reversing gear 318 is engaged with the second gear 314. The elongate inner member 306 is configured to be at least partially disposed within a lumen of the stent and extend along the sheath 302. A rack 320 includes a pin 326 that extends outside of the handle 300 and is engageable by a user to move the rack along a first axis parallel to the drive shaft axis to alternately engage one of the first gear 316 and the reversing gear 318. The rack 320 includes a trigger 330 extending outside of the handle 300, which is shown as a pistol-type trigger. The trigger 330 is engageable by the user to move the rack 320 along a second axis parallel to the deployment axis to rotate one of the first gear 316 and the reversing gear 318 when alternately engaged therewith. The pistol-type trigger 330 may be pulled proximally by a user to move the rack 320 in the proximal direction. The pin 326 connected to the rack 320 is disposed through the trigger 330, such that movement of the pin 326 and the rack 320 along the first axis through the trigger 330 allows the user to shift the rack 320 back and forth along the first axis to alternately engage the rack 320 with the first gear 316 and the reversing gear 318. Switching the rack 320 between the first gear 316 and the reversing gear 318 changes the direction that the deployment member 310 will move with a stroke of the trigger 330. For example, movement of the rack 320 along the second axis in a proximal direction when engaging the first gear 316 translates to movement of the deployment member 310 in the second direction, which may be distally to reconstrain the sheath 302 about the stent. Movement of the rack 320 along the second axis in a proximal direction when engaging the reversing gear translates to movement of the deployment member in the first direction, which may be proximally to deploy the stent. The rack 320 is moveable along the second axis parallel to the deployment axis to translate the rack 320 a predetermined stroke length. The stroke length is the length that the trigger 330 covers when moved proximally toward the handle 300 (e.g., a full trigger squeeze). The trigger 330 has a starting position. The deployment assembly 308 has one or more springs 328 (two illustrated in FIG. 3) cooperatively engaged with the rack 320 to apply a biasing force onto the rack 320 to return the trigger 330 to the starting position. Each spring 328 is disposed about a rod 303, the rod spanning from a grip of the handle 300 that terminates at an end feature 301 within the handle 300. The trigger 330 includes a trigger housing in which the rack 320 is disposed. The rods extend through the trigger housing, such that the housing with the rack 320 is slidably disposed along the rods to translate movement of the rack 320 along the second axis. The trigger housing is also sized to accommodate movement of the rack 320 along the first axis, e.g., when a user engages pin 326 to switch the direction of the deployment member 310 between retracting the sheath 302 to deploy the stent and moving the sheath to reconstrain the stent. In FIG. 3, the trigger 330 is shown in the starting position with the rack 320 engaging the reversing gear 318. The first one-way bearing and second one-way bearing prevent the first gear 316 and second gear 314 from transferring rotational forces to the drive shaft when the rack moves distally to the return to the starting position, such that as the spring 328 returns the trigger 330 to the starting position, no movement is transferred to the deployment member 310 regardless of which gear (the first gear or the reversing gear) is engaged. The stent may be held in place relative to the sheath 302 via the inner member 306. The constraining sheath 302 is operable with the inner member 306 to constrain the stent therebetween. The inner member 306 is shown extending through the elongate deployment member 310, but in other embodiments an inner member may extend alongside. The inner member 306 may extend up to and terminate in a luer fitting 332. Similar luer fittings may be used with other embodiments described herein and otherwise within the scope of the disclosure.

A scale 336 is disposed along the handle 300 such that a user may view and measure a distance that the elongate deployment member 310 has traveled, which may be calibrated to corresponds to an equivalent movement of the sheath 302 with respect to the stent. The scale 336 may include an indicator pointing to markings and/or the scale 336 may be translucent or slotted such that the deployment member 310 is visible along the scale 336 for the user to view and/or measure. A certain part of the scale 336 and/or the elongate deployment member 310 may be marked to indicate when the sheath 302 may be reaching a point where the sheath 302 can no longer reconstrain the stent. Similar scales, markings, and materials may be used with other embodiments described herein and otherwise within the scope of the disclosure. FIGS. 3A and 3B illustrate a similar arrangement for a deployment assembly of FIGS. 1 and 2, but are being used to highlight features such as the trigger 330, springs 328, scale 336, luer fitting 332, and to describe the deployment assembly in further detail.

In various embodiments within the scope of the present disclosure, a stroke length may be a distance that a trigger moves a rack with a full activation of the trigger. A stroke length may be less than a length of the stent. A stroke of a trigger may translate the elongate deployment member in a first direction (e.g., proximally along a deployment axis) in incremental steps. This movement with sheath attached to the deployment member retracts the sheath from about the stent to at least partially deploy the stent. A stroke of a trigger with the rack engaged with a reversing gear may move the deployment member proximally, in incremental steps, unconstraining or retracting the sheath from about the stent to at least partially deploy the stent. A stroke of a trigger may translate the elongate deployment member in a second direction (e.g., distally along the deployment axis) in incremental steps. This movement with the sheath attached to the deployment member at least partially constrains the stent within the sheath. A stroke of the trigger with the rack engaged with the first gear may move the deployment member distally, in incremental steps, at least partially constraining the stent within the sheath (e.g., reconstraining the stent within the sheath by moving the sheath back over a portion of the stent already deployed). The distance that the sheath moves relative to the stent, in a constraining or unconstraining fashion, may relate to the stroke length by a ratio that may be any suitable ratio depending on the gear configuration that is chosen, for example, 1:1, 1:2, 1:3, 1:4, 1:5, 1:6, 1:7, 1:8, 1:4, 1:9, 1:10, etc. It should be appreciated that a full activation of the trigger cannot deploy the stent from a fully constrained configuration within the constraining sheath to a deployed and fully unconstrained configuration so long as a stroke length of the trigger translates to a movement of the sheath that is less than the length of the stent. A deployment assembly may translate the elongate deployment member in incremental steps with each step being a stroke. Alternatively, each stroke may be made up of more than one incremental step for translating the deployment member. In various embodiments, a stroke length may be adjusted by changing the distance that the trigger moves, the length of the rack, the length of the rack that engages a gear, the travel distance of the rack, the ratio of gears translating rotation to the drive shaft, the size of the gears, the size of the gear teeth, and the like. Such stroke variations may be achieved by, for example, adjusting a stop block by manipulating an adjustable screw that impedes the stroke length by limiting the distance that the rack and or trigger may be moved. A cushioning zone may be configured in a device at a point where a stent is close to being deployed from the sheath and the sheath may not be able to reconstrain the stent. The cushioning zone may be a predetermined distance that the deployment member and the sheath may be retracted before reaching the point where the sheath can no longer be reconstrained about the stent. A portion of the length of distance traveled by the deployment member just before this point may be designated as the cushioning zone. Once the deployment member has been traveled a length of distance that enters the cushioning zone, a stop block or pin may impede the trigger and/or rack from completing the current stroke length. If desired at that point to fully deploy, the stop block or pin may be released with a release of the trigger, and one additional final pull of the trigger may then move the deployment member past the cushioning zone. When the retraction of a sheath reaches this cushioning zone, the user may be alerted and/or a new stroke may be required to get past the cushioning zone for deployment. Upon reaching the cushioning zone, the user may still reconstrain the stent and/or reposition the stent to a desired location. Additionally or alternatively, a setting may be configured on a device that engages the rack with a third gear on the drive shaft, such that a user may deploy the stent in one motion, without a stroke length restricted by the range of movement of the rack, should controlled deployment be unnecessary and/or too time consuming for the procedure. This may also be accomplished with a third length of teeth on the rack or the third gear having a higher ratio of stroke length to gear rotation than that of the first gear, second gear, reversing gear, first length of teeth, and second length of teeth. A rack may also have a setting that disengages the gears, such as a clip that moves the rack down off of the gears to allow manual manipulation of the deployment member for deployment and/or reconstrainment of the stent without use of a trigger and its confined stroke length.

Figure 4:
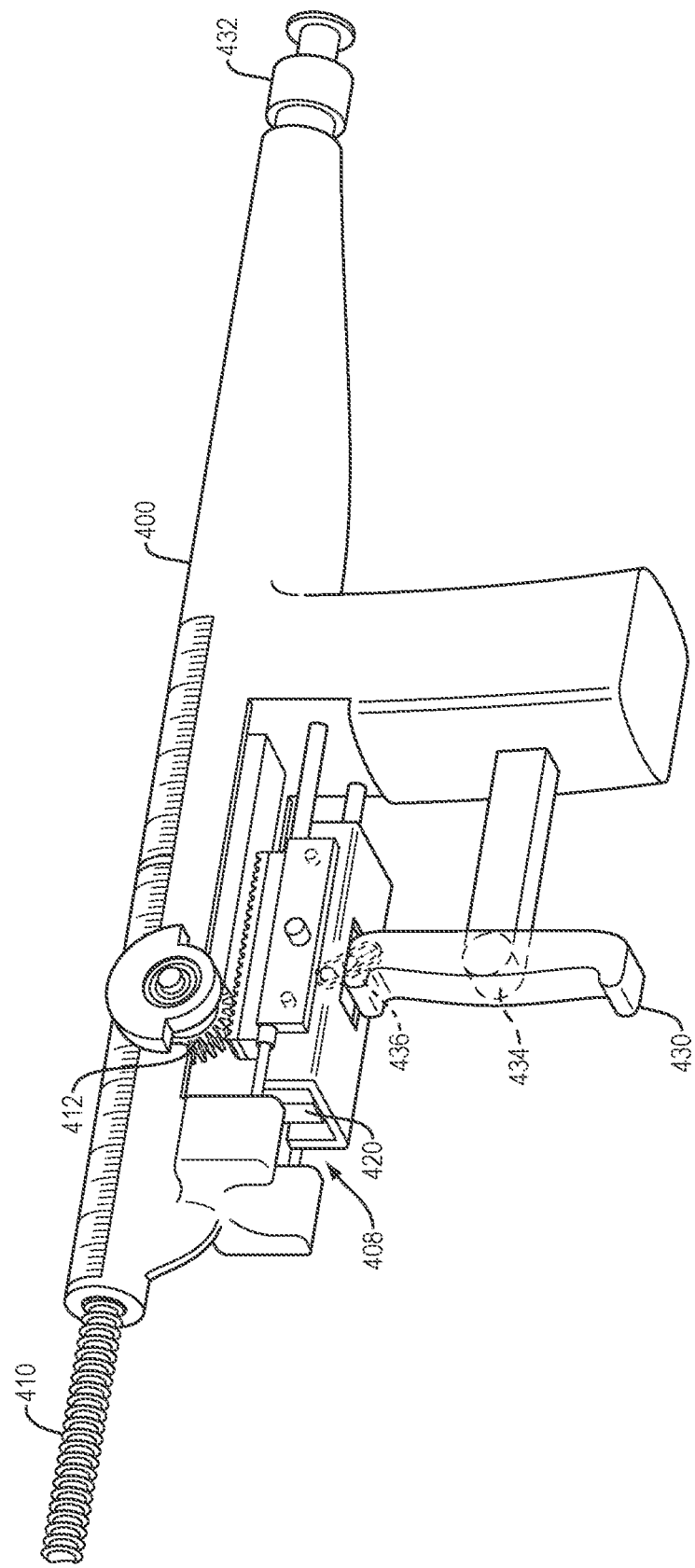
FIG. 4 illustrates a device having a handle and a deployment assembly with a seesaw-type trigger, in accordance with an embodiment of the present disclosure.

With reference to FIG. 4, an embodiment of a device for controlled delivery of a stent according to the present disclosure is illustrated, which includes a handle 400 containing a deployment assembly 408. A drive gear 412 is configured to engage the elongate deployment member 410 and has a deployment axis through the member 410. A drive shaft, having a drive shaft axis perpendicular to the deployment axis, is axially disposed through and coupled to the drive gear 412. A rack 420 is configured to engage the drive gear 412. The rack 420 is connected to a trigger 430 outside of the handle 400 to move the rack. The trigger 430 is a seesaw-type trigger that rotates about a fulcrum 434. The rack 420 is moveable along an axis parallel to the deployment axis. The top of the trigger 430 is pivotally connected to the rack 420 via a pin and slotted member 436. The slotted member 436 translates the rotation of the trigger 430 about the fulcrum 434 to the rack 420. In this way, the rotational arc segment that the trigger 430 travels is translated into linear movement of the rack 420 along the second axis parallel with the deployment axis. A user may rotate and/or pull the trigger 430 about the fulcrum 434 in a clockwise direction (e.g., by pulling proximally on the top portion of the trigger 430) to move the rack 420 in a proximal direction. A user may rotate the trigger 430 about the fulcrum 434 in a counter-clockwise direction (e.g., by pulling proximally on the bottom portion of the trigger 430) to move the rack 420 in a distal direction. The proximal and distal movement of the rack 420 is transferred to the drive gear 412 and to the elongate deployment member 410. With the elongate deployment member 410 attached to a restraining sheath, the user may constrain and unconstrain portions of the stent by rotating and/or pulling the trigger 430 about the fulcrum 434 in clockwise and counter-clockwise directions. The user, for example, may unconstrain the stent from the sheath by pulling on the bottom portion of the trigger 430 (the portion below the fulcrum 434) and may reconstrain the sheath over the stent by pulling on the top portion of the trigger 430, returning the trigger 430 to the starting position. FIG. 4 illustrates the rack 420 being at the proximal-most point of the stroke of the trigger 430 in the starting position. Distal motion of the rack 420 can fully deploy the stent from the sheath with a full pull of the bottom portion of the trigger 430. If desired, a user can reconstrain the sheath about the stent with a full pull of the top portion of the trigger 430 moving the deployment member 410 distally and the rack 420 to its proximal-most starting point. The stent may be held in place relative to the sheath via an inner member that is at least partially disposed within the stent and extending along the sheath. The inner member may extend through or alongside the elongate deployment member 410. The inner member may extend up to and terminate at a luer fitting 432. Some medical devices may be shorter in length than some of the stents described herein (e.g., such as stent 104), and may require less than a stroke length for unconstrainment and reconstrainment. Embodiments like the one illustrated in FIG. 4 may have a shorter stroke length in the proximal or distal direction than, for example, the embodiments shown in FIGS. 1 through 3B. Additionally, there may be no need for a user to take the additional step of moving the rack 420 along a first axis parallel to a drive shaft axis to engage a gear other than the drive gear 412 because the deployment member 410 may be moved proximally or distally with the rotation of the drive gear 412 unconstraining or constraining, respectively, the entirety of the stent in one stroke.

In various embodiments described here or otherwise within the scope of the present disclosure, the trigger may be a variety of mechanisms for moving a rack. For example, the trigger may be a pistol-type trigger, a seesaw-type trigger, a thumb wheel, hand pump, jack level, or the like. FIG. 4 shows a trigger arrangement that may be implemented similarly in a thumb wheel. For example, a trigger that is a thumb wheel may be rotated to move the rack along the second axis in a first direction that translates to movement of the deployment member in a second opposing direction. Rotation of the thumb wheel in an opposite direction moves the rack along the second axis in the second direction that translates to movement of the deployment member in the first opposing direction. An embodiment of a thumb wheel may alternatively be configured similar to the pistol-type trigger deployment assembly of FIGS. 1-3B, and optionally have springs similar to that of FIG. 3A, or a rotary spring within the wheel, that operates only to move the rack proximally by a predetermined stroke length. A rotation of a trigger that is a thumbwheel may be a rotation of a number of degrees equal to a stroke length of the trigger and/or rack. The number of degrees of rotation of the thumb wheel may translate to a portion of the stroke length and may include an auditory signal (e.g., a "click") that alerts the user to a certain length of distance that the sheath has been moved relative to full deployment or reconstrainment of the sheath. For example, each "click" could be about 30° corresponding to about 5 mm of sheath movement. In other embodiment the amount of degree of rotation of the wheel may be matched to the movement of the sheath, as desired for the particular application and configuration of stent. The deployment member may be translated in incremental steps that may be a portion of a stroke length or an entire stroke length. A trigger may be motorized and may be controlled by a computer with pre-programmed instructions for the stent to a location and/or deploying the stent. Embodiments having a trigger and a handle may allow a user to insert and deploy a stent using only one hand. This may allow the user to maintain tension on the stent, reduce the need for additional user s, and/or allow the user to operate another device such as, for example, a scope or the like. A trigger may have a safety lock that prevents the trigger from moving and possibly inadvertent stent deployment.

Figure 5:
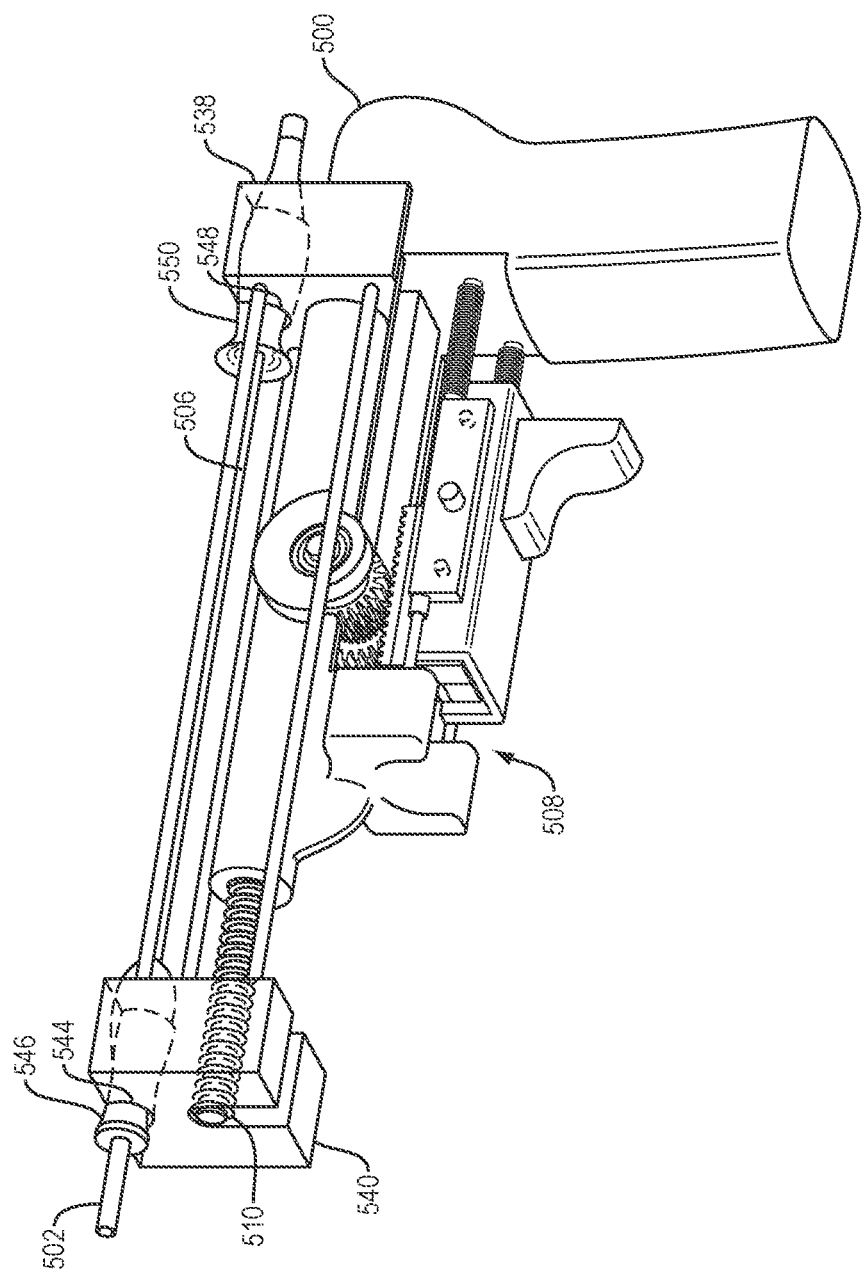
FIG. 5 illustrates a device configured to accommodate other existing stent deployment devices, in accordance with an embodiment of the present disclosure.

With reference to FIG. 5, an embodiment of a device for controlled delivery of a stent according to the present disclosure is illustrated, which includes a handle 500 containing a deployment assembly 508 similar to the arrangement described above with respect to FIGS. 2, 3A, and 3B. A distal holder 540 is disposed onto an elongate deployment member 510. A proximal holder 538 is disposed onto the handle 500. The distal holder 540 moves proximally and distally with the proximal and distal movement of the elongate deployment member 510. The distal holder 540 has an impression 544 configured to accept a distal handle 546 that is attached to a constraining sheath 502. The proximal holder 538 has an impression 548 configured to accept a proximal handle 550 that is attached to an inner member 506 disposed through the distal handle 546 and the constraining sheath 502. The impressions 544 and 548 may have shoulders that create a reversible snap-fit arrangement with the handles 546 and 550. Such a device can be used with conventional delivery devices to retrofit a device for controlled delivery. With the distal handle 546 within the distal holder 540 and the proximal handle 550 within the proximal holder 538, the distal holder 540 may be moved with respect to the proximal holder 538 to move the sheath 502 with respect to the stent and the inner member 506. During operation, the proximal handle 550 and inner member 506 remain stationary with respect to the distal handle 546 and the sheath 502. The inner member 506 may hold the stent stationary during movement of the sheath 502 for unconstraining and reconstraining of the stent via movement of the elongate deployment member 510, the distal holder 540, and the distal handle 546.

Figure 6:
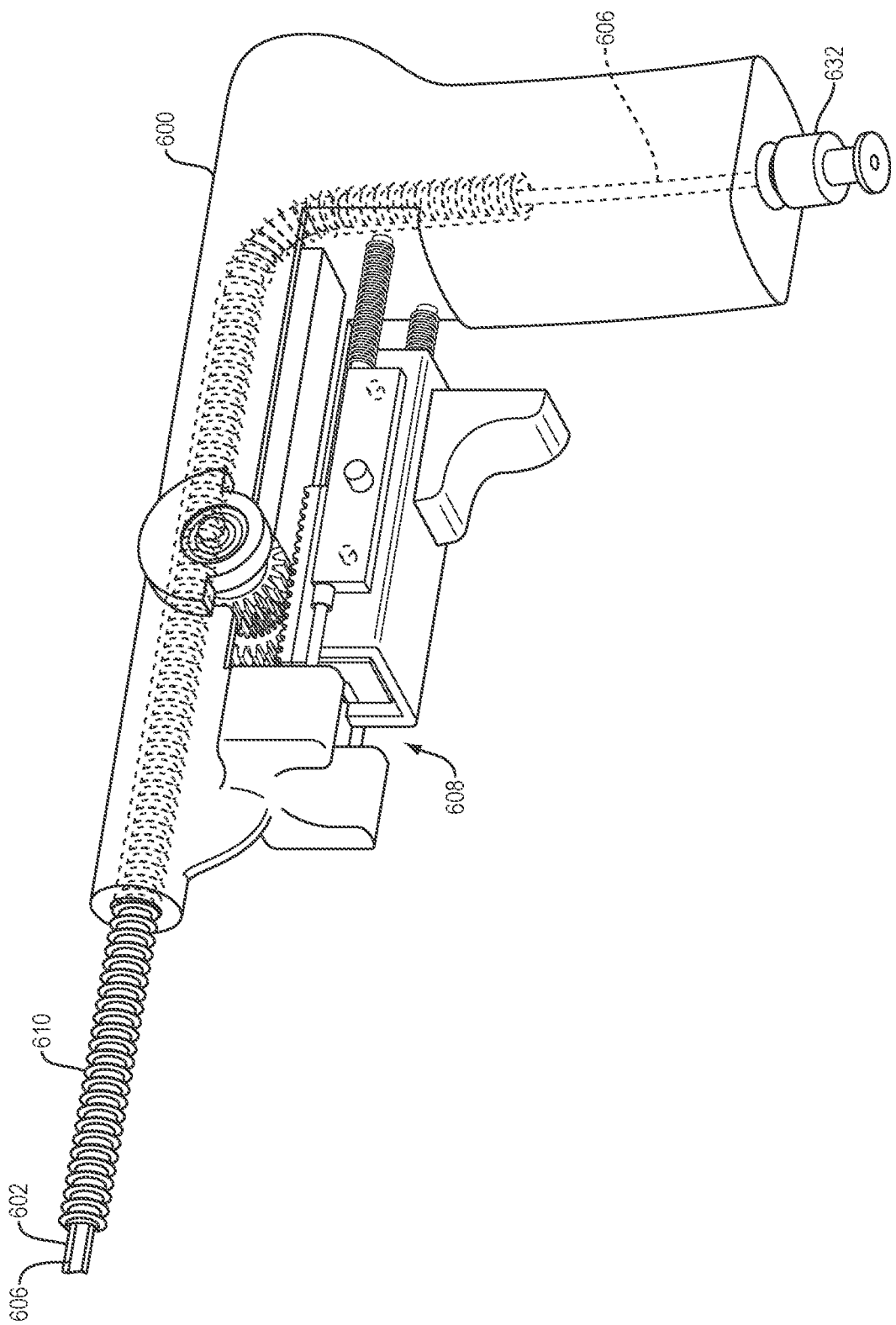
FIG. 6 illustrates a further device with an elongate deployment member, in accordance with an embodiment of the present disclosure.

With reference to FIG. 6, an embodiment of a device for controlled delivery of a stent according to the present disclosure is illustrated, which includes a handle 600 containing a deployment assembly 608. An elongate deployment member 610 is at least semi-flexible such that it retracts in a proximal direction towards the proximal end of the handle 600, and then towards a bottom portion of the handle 600 towards a luer fitting 632. A proximal end of a sheath 603 is connected to the distal end of the deployment member 610. An elongate inner member 606 is at least partially disposed within a lumen of the stent and extends along the sheath 602, and through the deployment member 610 to the luer fitting 632.

Figure 7A:
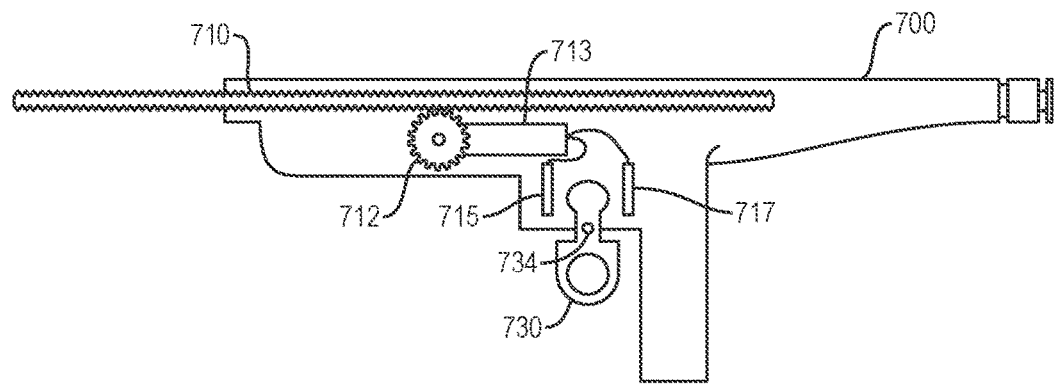
FIG. 7A illustrates a left view of a device including a motor and a deployment member, in accordance with an embodiment of the present disclosure.
Figure 7B:
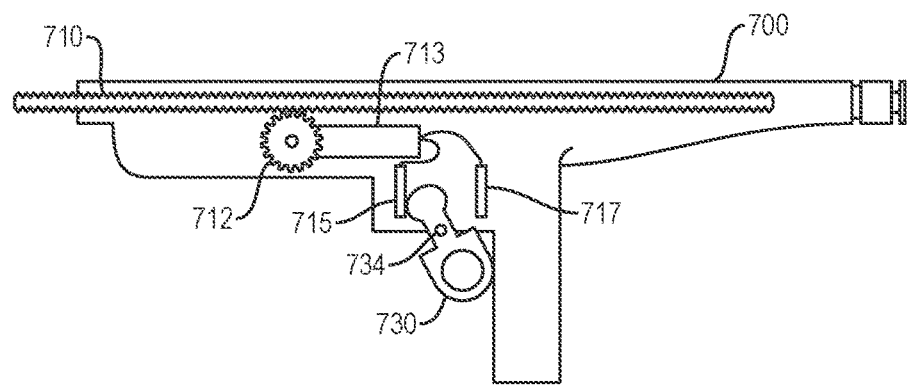
FIG. 7B illustrates the device of FIG. 7A with the deployment member in a position that is more proximal than the position of the deployment member in FIG. 7A.
Figure 7C:
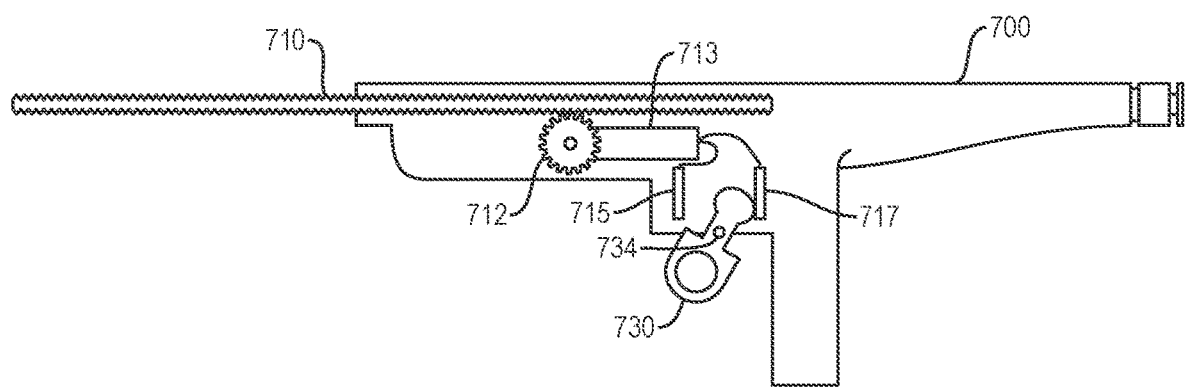
FIG. 7C illustrates the device of FIGS. 7A and 7B with the deployment member in a position that is more distal than the position of the deployment member in FIGS. 7A and 7B.

With reference to FIGS. 7A-7C, an embodiment of a device for controlled delivery of a stent according to the present disclosure is illustrated, which includes a motor 713 connected to a drive gear 712 to move a deployment member 710 in a proximal or distal direction. The direction and activation of the motor 713 may be driven by a user-operated ring-shaped trigger 730 in which a finger may be inserted and pushed and/or pulled to move the trigger distally and proximally, respectively. A medical device, such as a stent, may be unconstrained by the user pulling on the trigger 730 towards the handle 700 and about the trigger pin 734 (e.g., FIG. 7B), which activates a first switch 715 configured to drive the motor 713 in a first direction. The medical device may be reconstrained by the user pushing on the trigger 730 away from the handle 700 (e.g., FIG. 7C), which activates a second switch 717 configured to drive the motor 713 in a second direction. The first direction may be to drive the deployment member proximally, and the second direction may be to drive the deployment member distally. The motor drives the drive gear 712, which moves the deployment member 710. The motor may be battery operated, with the batteries stored within the handle 700 or in a compartment external to the handle 700 for easy access. The motor 713 may alternatively be powered by an AC source in combination with an AC/DC transformer external to the handle 700 and connected to a power cord.

In variations of the embodiments described here or otherwise within the scope of the present disclosure, a method of delivering a stent may include inserting a stent into a patient to a deployment location. The stent may be disposed on an inner member and constrained within a sheath. The sheath may have a proximal end connected to an end of an elongate deployment member. The deployment member may extend along a deployment axis. The sheath may be at least partially retracted proximally from about the stent in incremental strokes, which corresponds to proximal movement of the deployment member along the deployment axis. A single stroke may retract the sheath a distance less than a length of the stent. Retracting the sheath from about the stent may include moving a rack proximally along an axis parallel to the deployment axis. The rack may communicate with one or more gears to transfer the proximal movement of the rack, through rotation of the gears, to the proximal movement of the deployment member. The stent may be at least partially reconstrained within the sheath in incremental strokes, which may correspond to a distal movement of the deployment member along the deployment axis. A single stroke may reconstrain the stent within the sheath a distance less than a length of the stent. Reconstraining the stent within the sheath may include moving a rack proximally along the axis parallel to the deployment axis. The rack may communicate with one or more gears to transfer the proximal movement of the rack through rotation of the gears, to the distal movement of the deployment member. Retracting the sheath and reconstraining the stent within the sheath may be by the same proximal movement of the rack and may be by switching the rack from engaging one gear of the one or more gears to engaging another gear of the one or more gears. The sheath may be retracted and may reconstrain the stent within the sheath by movement of a trigger that is in communication with the rack. The trigger may be a pistol-type trigger, thumb wheel, or seesaw-type trigger. The deployment member may be one of removably connected to the sheath, fixedly connected to the sheath, or integral with the sheath. The deployment member may be removably engageable with the sheath.

All of the devices and/or methods disclosed and claimed herein can be made and executed without undue experimentation in light of the present disclosure. While the devices and methods of this disclosure have been described in terms of certain embodiments, it may be apparent to those of skill in the art that variations can be applied to the devices and/or methods and in the steps or in the sequence of steps of the methods described herein without departing from the concept, spirit and scope of the disclosure. All such similar substitutes and modifications apparent to those skilled in the art are deemed to be within the present disclosure.

What is claimed is:

1. A device for controlled delivery of a stent, comprising:
   a handle;
   an elongate inner member having a proximal end and a distal end, the inner member disposed distal to the handle and configured to extend within a lumen of the stent;
   a constraining sheath having a proximal end and a distal end, the sheath extending about the inner member and operable with the inner member to constrain the stent therebetween; and
   a deployment assembly disposed within the handle, comprising:
      an elongate deployment member having a proximal end, a distal end, and a deployment axis extending therealong, the distal end of the deployment member coaxially connected to the proximal end of the constraining sheath;
      a drive gear, wherein the assembly is operable to laterally translate the elongate deployment member in incremental steps along the deployment axis in a first direction via direct engagement of the drive gear with the elongate deployment member to at least partially deploy the stent, and is operable to laterally translate the deployment member in incremental steps along the deployment axis in a second direction via direct engagement of the drive gear with the elongate deployment member to at least partially constrain the stent;
      a drive shaft having a drive shaft axis perpendicular to the deployment axis, the drive shaft axially disposed through and coupled to the drive gear;
      a first gear axially disposed about and coupled to the drive shaft;
      a second gear axially disposed about and coupled to the drive shaft, the second gear spaced apart from the first gear along the drive shaft axis;
      a reversing gear in communication with the second gear; and
      a rack configured to alternately engage the first gear and the reversing gear.

2. The device of claim 1, further comprising:
   a first one-way bearing coupled to the first gear and axially disposed about and coupled to the drive shaft, the first bearing configured to prevent the first gear from imparting a rotary motion to the drive shaft that translates the deployment member in the first direction; and
   a second one-way bearing coupled to the second gear and axially disposed about and coupled to the drive shaft, the second bearing configured to prevent the second gear from imparting a rotary motion to the drive shaft that translates the deployment member in the second direction.

3. The device of claim 1, wherein the rack has a first length of teeth configured to engage the first gear and a second length of teeth configured to engage the reversing gear, wherein the first length and the second length are parallel to the deployment axis and to each other.

4. The device of claim 3, wherein the first length is spaced apart from the second length a distance that is different than a distance between the first gear and the second gear, such that the rack can only alternately engage the first length with the first gear or the second length with the reversing gear.

5. The device of claim 1, wherein the rack is moveable back and forth along a first axis parallel to the drive shaft axis to alternately engage one of the first gear and the reversing gear, and wherein the rack is moveable back and forth along a second axis parallel to the deployment axis to rotate one of the first gear and the reversing gear when alternately engaged therewith.

6. The device of claim 5, wherein the rack includes a trigger extending outside of the handle, the trigger engageable by a user to move the rack along the second axis, wherein movement of the rack along the second axis in a proximal direction when engaging the first gear translates to movement of the deployment member in the second direction, and wherein movement of the rack along the second axis in a proximal direction when engaging the reversing gear translates to movement of the deployment member in the first direction.

7. The device of claim 6, wherein the trigger has a starting position and the deployment assembly further comprises one or more springs cooperatively engaged with the rack to apply a biasing force onto the rack to return the trigger to the starting position.

8. The device of claim 5, wherein the rack is moveable in the proximal direction along the second axis a predetermined stroke length.

9. The device of claim 8, wherein the stroke length is less than the length of the stent.

10. The device of claim 1, wherein translating the elongate deployment member in the first direction at least partially deploys the stent from within the sheath.

11. A system for controlled stent delivery comprising:
    a self-expanding stent;
    an elongate inner member having a proximal end and a distal end, the inner member disposed distal to the handle and configured to extend within a lumen of the stent;
    a constraining sheath having a proximal end and a distal end, the sheath extending about the inner member and operable with the inner member to constrain the stent therebetween; and a handle containing a deployment assembly, the deployment assembly comprising:
- an elongate deployment member having a proximal end, a distal end, and a deployment axis extending therealong, the distal end of the deployment member connected to and coaxial with the proximal end of the constraining sheath;
- a drive gear, wherein the assembly is operable to laterally translate the deployment member in incremental steps along the deployment axis in a first direction via direct engagement of the drive gear with the elongate deployment member along a rack to at least partially deploy the stent, and is operable to laterally translate the deployment member in incremental steps along the deployment axis in a second direction via direct engagement of the drive gear with the elongate deployment member along the rack to at least partially constrain the stent;
- a drive shaft, having a drive shaft axis perpendicular to the deployment axis, the drive shaft axially disposed through and coupled to the drive gear;
- a first gear axially disposed about and coupled to the drive shaft;
- a second gear axially disposed about and coupled to the drive shaft, the second gear spaced apart from the first gear along the drive shaft axis;
- a reversing gear in communication with the second gear;
- the rack configured to alternately engage the first gear and the reversing gear; and
- a trigger configured to translate the rack proximally and distally.

12. The system of claim 11, further comprising:
a first one-way bearing coupled to the first gear and axially disposed about and coupled to the drive shaft, the first bearing configured to prevent the first gear from imparting a rotary motion to the drive shaft that translates the deployment member in the first direction; and
a second one-way bearing coupled to the second gear and axially disposed about and coupled to the drive shaft, the second bearing configured to prevent the second gear from imparting a rotary motion to the drive shaft that translates the deployment member in the second direction.

13. The system of claim 11, wherein the rack is moveable back and forth along a first axis parallel to the drive shaft axis to alternately engage one of the first gear and the reversing gear, and wherein the rack is moveable back and forth along a second axis parallel to the deployment axis to rotate one of the first gear and the reversing gear when alternately engaged therewith.

14. The system of claim 13, wherein the rack is moveable in the proximal direction along the second axis a predetermined stroke length.

15. A method of delivering a stent comprising:
- inserting a stent into a patient to a deployment location, the stent disposed on an inner member and constrained within a sheath, the sheath having a proximal end connected to an end of an elongate deployment member, the elongate deployment member extending along a deployment axis;
- at least partially retracting the sheath proximally from about the stent in predetermined incremental strokes, which corresponds to lateral proximal movement of the elongate deployment member along a rack based on direct engagement of a drive gear with the elongate deployment member, wherein a single stroke retracts the sheath a distance less than a length of the stent;
- reconstraining, at least partially, the stent within the sheath in predetermined incremental strokes, which correspond to a distal movement of the elongate deployment member along the deployment axis, wherein a single stroke reconstrains the stent within the sheath a distance less than a length of the stent,
- wherein retracting the sheath from about the stent further comprises moving the rack proximally along an axis parallel to the deployment axis, and wherein the rack communicates with one or more gears to transfer the proximal movement of the rack, through rotation of the gears, to the proximal movement of the elongate deployment member, and
- wherein reconstraining the stent within the sheath further comprises moving the rack proximally along the axis parallel to the deployment axis, and wherein the rack communicates with one or more gears to transfer the proximal movement of the rack, through rotation of the gears, to the distal movement of the elongate deployment member.

* * * * *